United States Patent [19]

Strupczewski

[11] Patent Number: 4,528,292
[45] Date of Patent: Jul. 9, 1985

[54] ANTIHYPERTENSIVE 1,2-BENZISOTHIAZOLE PIPERIDINES

[75] Inventor: Joseph T. Strupczewski, Flemington, N.J.

[73] Assignee: Hoechst-Roussel Pharmaceuticals Inc., Somerville, N.J.

[21] Appl. No.: 603,264

[22] Filed: Apr. 23, 1984

[51] Int. Cl.³ .................. C07D 417/04; A61K 31/425
[52] U.S. Cl. ..................................... 514/321; 546/198
[58] Field of Search ........................ 546/198; 424/267

[56] References Cited

U.S. PATENT DOCUMENTS 4,355,037 10/1982 Strupczewski et al. ............ 546/198

OTHER PUBLICATIONS

Winthrop et al., "J. Org. Chem.", vol. 24, pp. 1936-1939, (1956).
Steindorff, "Chem. Ber.", vol. 37, pp. 963-966, (1904).
March, "Advanced Organic Chemistry: Reactions, Mechanisms and Structure", (McGraw-Hill) (1968), p. 664.

*Primary Examiner*—Robert T. Bond
*Attorney, Agent, or Firm*—Tatsuya Ikeda

[57] ABSTRACT

There are described novel antihypertensive 1,2-benzisothiazole piperidines of the formula

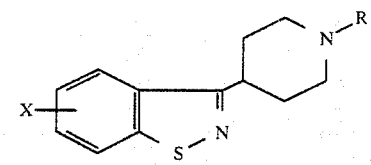

where X is hydrogen, halogen, loweralkoxy, loweralkyl, nitro, amino or trifluoromethyl; and R is

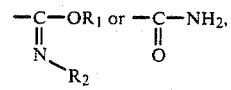

$R_1$ being loweralkyl, aryl, aralkyl, cycloalkylloweralkyl or a loweralkyl substituted with an amino, loweralkylamino or diloweralkylamino, and $R_2$ being hydrogen, loweralkyl or aryl; antihypertensive compositions comprising said compounds or pharmaceutically acceptable acid addition salts thereof; and methods for synthesizing the same.

13 Claims, No Drawings

ANTIHYPERTENSIVE 1,2-BENZISOTHIAZOLE PIPERIDINES

This invention relates to novel antihypertensive 1,2-benzisothiazole piperidines of the formula

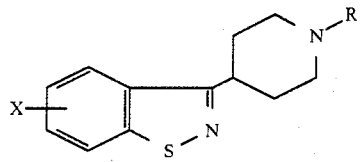

where X is hydrogen, halogen, loweralkoxy, loweralkyl, nitro, amino or trifluoromethyl; and R is

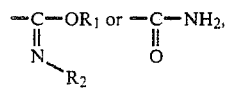

$R_1$ being loweralkyl, aryl, aralkyl, cycloalkylloweralkyl or a loweralkyl substituted with an amino, loweralkylamino or diloweralkylamino, and $R_2$ being hydrogen, loweralkyl or aryl; antihypertensive compositions comprising said compounds or pharmaceutically acceptable acid addition salts thereof; and methods for synthesizing said compounds.

To the best of our knowledge the compounds of the present invention have not been described or suggested.

Throughout the specification and the appended claims, a given chemical formula or name shall encompass all stereoisomers thereof where such isomers exist.

The term "lower" shall mean 1 to 6 carbon atoms. The term "aralkyl" shall mean a loweralkyl substituted with an aryl group. The term "cycloalkyl" shall mean an alicyclic group having 3-6 carbon atoms. The term halogen shall mean fluorine, chlorine, bromine or iodine unless otherwise indicated.

The compounds of the present invention are prepared by following one or more of the following steps described below in which the definitions of X, R, $R_1$ and $R_2$ are as given above unless noted to the contrary.

STEP A

Compound of Formula II is cyclized in the presence of ammonia and sulphur to afford a compound of Formula III.

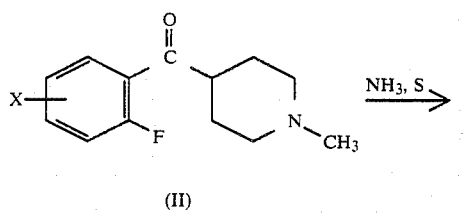

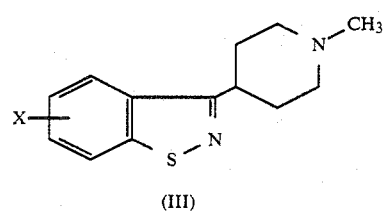

Said cyclization is conveniently conducted by treating Compound II with sulfur in an alkanol saturated with ammonia at an elevated temperature of about 75° to about 150° in a suitable reaction vessel, e.g., an autoclave. Suitable alkanols include glycol monoalkyl ethers such as ethylene glycol monomethyl ether and the like. Ethylene glycol monomethyl ether is a preferred alkanol. A temperature of about 130° C. is a preferred reaction temperature. Synthesis of Compound II is described in U.S. Pat. No. 4,355,037.

STEP B

Compound III is cyanated to afford a compound of Formula IV.

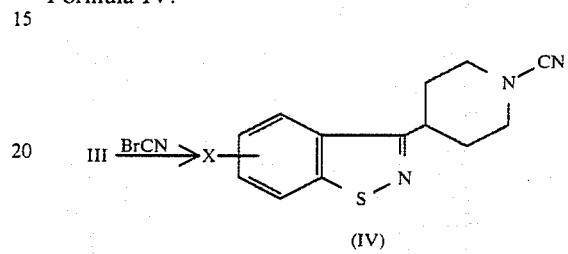

Said cyanation of Compound III is accomplished by contacting it with a cyanogen halide such as cyanogen bromide or cyanogen chloride, preferably cyanogen bromide, in a suitable solvent such as dichloromethane, trichloromethane or dichloroethane, preferably trichloromethane, in the presence of an inorganic base such as sodium or potassium carbonate or sodium or potassium bicarbonate, preferably potassium carbonate. The reaction proceeds readily at moderate temperatures. To facilitate the conversion, however, an elevated temperature, i.e., the reflux temperature of the system, is employed.

STEP C

Compound IV is reacted with an alcohol of the formula $R_1OH$ in the presence of an alkali metal cyanide such as potassium cyanide to afford a compound of Formula V.

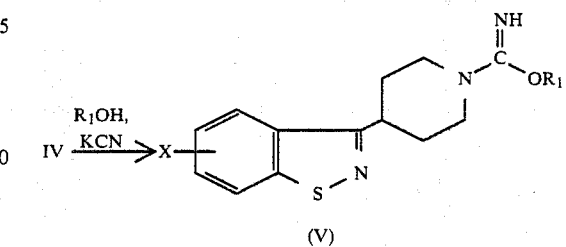

Ordinarily the reaction is conducted in the presence of alkali metal cyanide such as potassium cyanide and an excess amount of the alcohol $R_1OH$, which also works as a reaction medium. A typical reaction condition is refluxing the reaction mixture for several hours and then further continuing the reaction at ambient temperature for 10–20 hours.

STEP D

As an alternative to STEP C, Compound IV is reacted with an alcohol of the formula $R_1OH$ in the presence of (usually only catalytic amount) of an alkali metal alkoxide of formula $MOR_1$ where M is an alkali metal, preferably sodium. Usually sodium metal is added to an excess amount of an alcohol of formula $R_1OH$ to form the sodium alkoxide of formula $NaOR_1$. Thereafter Compound IV is added to the mixture and if necessary the mixture is heated slightly until a uniform solution is obtained. Then the reaction is continued typically at an ambient temperature for 16 hours, for instance.

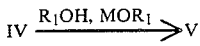

STEP E

Compounds of Formula VI below are prepared by use of the reaction sequence described below.

Compound IV is hydrolyzed to afford Compound VII.

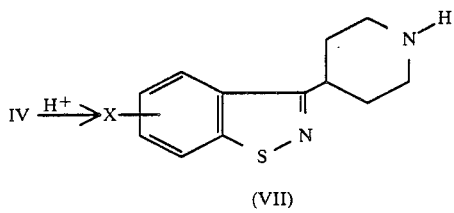

Said hydrolysis is conducted, for instance, by refluxing compound IV in 25% aqueous solution of sulfuric acid for several hours.

Compound VII is reacted with an isocyanate $R_2NCO$ to afford a urea derivative of Formula VIII.

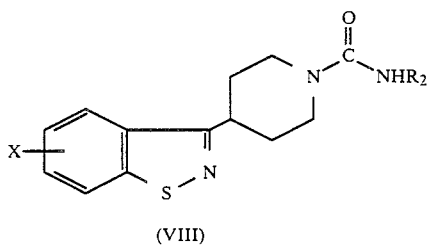

Said reaction is typically conducted in a suitable medium such as benzene or toluene and refluxing the reaction mixture for 1-24 hours.

Compound VIII is chlorinated to afford Compound IX by use of, for instance, phosphorus pentachloride.

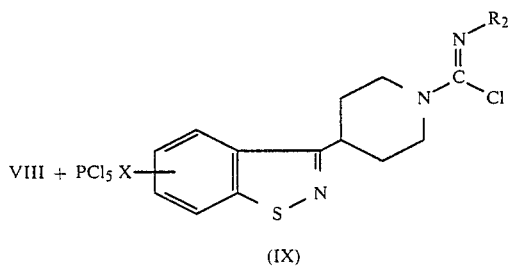

Said chlorination reaction is conducted by refluxing a mixture consisting of Compound VIII, $PCl_5$ and a suitable medium such as chlorobenzene until the evolution of hydrogen chloride ceases.

Finally, Compound IX is reacted with the equivalent amount of an alkali metal alkoxide of an alcohol $R_1OH$ to afford Compound VI (In the equation below, M is an alkali metal).

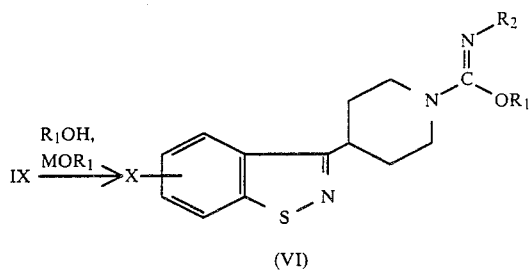

Said reaction is conducted typically in either the alcohol $R_1OH$ as a solvent or in an inert solvent such as toluene or DMF at reflux temperature (in the case of $R_1OH$ or toluene, for instance) or an elevated temperature (in the case of DMF, for instance) for a suitable length of time such as 0.5-24 hours.

STEP F

Compound X is obtained by the hydrolysis of Compound V.

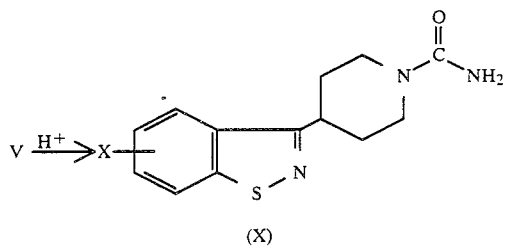

Typically said hydrolysis reaction is conducted in a strongly acidic medium such as 48% aqueous HBr and stirring the mixture at an elevated temperature such as 90° C. for 10-20 hours.

All other starting materials shown above are either known compounds or easily prepared by routine methods known to the art from readily available materials.

The 1,2-benzisothiazole piperidines of the present invention depicted by Formula (I) are useful as antihypertensive agents due to their ability to depress blood pressure in mammals. Antihypertensive activity is measured in the spontaneous hypertensive rat by the indirect tail cuff method described in "Methods in Pharmacology", A. Schwartz, Ed., Vol. I, Appleton-Century Crofts, New York, N.Y., 1971, p. 135. In this procedure a group of five animals are treated orally for three days with the test compound in relation to a control group of the same number. The drop in blood pressure in measured on the third day following administration. The antihypertensive activities of some of the compounds of this invention, expressed as a decrease in mean arterial blood pressure (in mm Hg), are given in Table I.

TABLE 1

| Compound | ANTIHYPERTENSIVE ACTIVITY | |
|---|---|---|
| | Dose mg/kg p.o. | Blood Pressure Drop mm Hg |
| 4-(1,2-Benzisothiazol-3-yl)piperidine-1-carboximidic acid methyl ester | 3 | 63 |

TABLE 1-continued

ANTIHYPERTENSIVE ACTIVITY

| Compound | Dose mg/kg p.o. | Blood Pressure Drop mm Hg |
|---|---|---|
| 3-(1-Aminocarbonyl-4-piperidinyl)-1,2-benzisothiazole hydrobromide | 50 | 26 |
| 4-(1,2-Benzisothiazol-3-yl)piperidine-1-carboximidic acid ethyl ester hydrochloride | 50 | 41 |
| 4-(1,2-Benzisothiazol-3-yl)piperidine-1-carboximidic acid cyclopropylmethyl ester | 50 | 18 |
| 4-(1,2-Benzisothiazol-3-yl)piperidine-1-carboximidic acid 2-propyl ester | 50 | 22 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parentera preparation can be enclosed in disposable syringes or multiple dose vials made of glass or plastic.

Examples of the compounds of this invention include:
4-(1,2-Benzisothiazol-3-yl)piperidine-1-carboximidic acid methyl ester;
3-(1-Aminocarbonyl-4-piperidinyl)-1,2-benzisothiazole;
4-(1,2-Benzisothiazol-3-yl)piperidine-1-carboximidic acid ethyl ester;
4-(1,2-Benzisothiazol-3-yl)piperidine-1-carboximidic acid cyclopropylmethyl ester;
4-(1,2-Benzoisothiazol-3-yl)piperidine-1-carboximidic acid 2-propyl ester; and
4-(1,2-Benzisothiazol-3-yl)piperidine-1-carboximidic acid 2-diethylaminoethyl ester.

The following examples are given for illustrative purposes and are not to be considered as limiting the invention disclosed herein. All temperatures are given in degrees Celsius.

EXAMPLE 1

3-(1-Cyano-4-piperidinyl)-1,2-benzisothiazole

To a stirred mixture of CNBr (5.9 g, 0.056 mole), $K_2CO_3$ (8.6 g) and $CHCl_3$ (80 ml) was added dropwise 3-(1-methyl-4-piperidinyl)-1,2-benzisothiazole (11.0 g, 0.051 mole) in $CHCl_3$ (30 ml). The mixture was stirred and refluxed for 4 hours and thereafter cooled and filtered. The filtrate was concentrated in vacuo to a solid. The solid was triturated with hexane and collected to yield 13.5 g of the desired compound. Recrystallization from MeOH—$H_2O$ (twice) yielded 4.5 g (36%) of the benzisothiazole, m.p. 118°–120°.

ANALYSIS: Calculated for $C_{13}H_{13}N_3S$: 64.17%C, 5.38%H, 17.27%N; Found: 63.94%C, 5.35%H, 17.37%N.

EXAMPLE 2

4-(1,2-Benzisothiazol-3-yl)piperidine-1-carboximidic acid methyl ester

A mixture of 3-(1-cyano-4-piperidinyl)-1,2-benzisothiazole (11.7 g, 0.048 mole), KCN (3.1 g) and MeOH (145 ml) was stirred and refluxed for 4 hours, and then stirred at ambient temperature for 14 hours. The MeOH was removed in vacuo and the residue diluted with water. The aqueous suspension was extracted with chloroform and the chloroform extract was washed with water and dried over MgSO$_4$. Thereafter, the chloroform was evaporated in vacuo to yield 12.4 g of a solid. Recrystallization from EtOAc yielded 6.0 g (45.2%) of a solid. An analytical sample was obtained by a second recrystallization of a 3.5 g sample. The resultant solid (2.6 g) had a melting point of 144°–146° C.

ANALYSIS: Calculated for C$_{14}$H$_{17}$N$_3$OS: 61.06%C, 6.22%H, 15.24%N, Found: 60.84%C, 6.17%H, 15.20%N.

EXAMPLE 3

3-(1-Amninocarbonyl-4-piperidinyl)-1,2-benziso-thiazole hydrobromide

A crude sample of 4-(1,2-benzisothiazol-3-yl)piperidine-1-carboximidic acid methyl ester (7.7 g, 0.028 mole) was added to 70 ml of 48% aqueous HBr and the mixture was stirred and heated at about 90° for 16 hours. After cooling the mixture to ambient temperature, a precipitate was collected, washed with acetone and dried to afford 8.4 g of a solid. The material was recrystallized twice from isopropanol-ether to yield 3.7 g (38.6%) of the compound as hydrobromide salt, m.p. 169°–170°.

ANALYSIS: Calculated for C$_{13}$H$_{15}$N$_3$OS.HBr: 45.63%, 4.71%H, 12.28%N; Found: 45.77%C, 4.74%H, 12.17%N.

EXAMPLE 4

4-(1,2-Benzisothiazol-3-yl)piperidine-1-carboximidic acid ethyl ester hydrochloride A mixture of 3-(1-cyano-4-piperidinyl)-1,2-benzoisothiazole (4.0 g, 0.016 mole), KCN (1.1 g) and EtOH (50 ml) was stirred and refluxed for 4 hours and then stirred at ambient temperature for 14 hours. The EtOH was evaporated in vacuo and the residue diluted with water. The aqueous suspension was extracted with CH$_2$Cl$_2$, and the organic phase was washed with water and dried (MgSO$_4$). The solvent was evaporated in vacuo to yield 3.4 g of a solid. The solid was treated with ethereal HCl to yield 3.0 g of hydrochloride salt. Recrystallization of the salt from EtOH—Et$_2$O gave 2.2 g (38%) of the desired compound, m.p. 148°–150° (evolution of gas).

ANALYSIS: Calculated for C$_{15}$H$_{19}$N$_3$OS.HCl: 55.30%C, 6.19%H, 12.90%N; Found: 55.20%C, 6.13%C, 13.05%N.

EXAMPLE 5

4-(1,2-Benzisothiazol-3-yl)piperidine-1-carboximidic acid cyclopropylmethyl ester To 15 ml of cyclopropylcarbinol was added 0.05 g of Na metal. After the evolution of hydrogen gas ceased, 3-(1-cyano-4-piperidinyl)-1,2-benzisothiazole (4.0 g, 0.016 mole) was added. The temperature was raised to 60° C. to obtain a solution. Heat was removed and the reaction mixture was stirred at ambient temperature for 16 hours. Dry ice was added to the reaction mixture to destroy the excess alkoxide and the mixture was poured into water. The aqueous mixture was extracted with EtOAc. The EtOAc extract was washed with water and dried over MgSO$_4$, and the solvent was removed in vacuo to leave an oil. The oil was triturated with hexane to yield 4.0 g of a solid. The solid was recrystallized twice from isopropyl ether to yield 2.4 g (46.3%) of the imidate as a solid, m.p. 85°–87°.

ANALYSIS: Calculated for C$_{17}$H$_{21}$N$_3$OS: 64.74%C, 6.71H, 13.32%N; Found: 64.99%C, 6.61%H, 13.30%N.

EXAMPLE 6

4-(1,2-Benzisothiazol-3-yl)piperidine-1-carboximidic acid 2-propyl ester

To a stirred solution of isopropanol-sodium isopropoxide (prepared from 0.05 g of Na metal and 20 ml of isopropanol) was added 3-(1-cyano-4-piperidinyl)-1,2-benzisothazole (4.0 g, 0.016 mole). The mixture was brought to reflux, and when the solid went into solution heating was discontinued. The reaction mixture was stirred at ambient temperature for 14 hours, and then dry ice was added to quench the residual alkoxide. The isopropanol was removed under reduced pressure, and the resultant viscous oil was diluted with water. The aqueous mixture was extracted with chloroform, and the chloroform extract was washed with brine and dried over MgSO$_4$. The solvent was removed in vacuo to yield a solid. Recrystallization of the solid from EtOAc yielded 3.0 g (61.8%) of the imidate, m.p. 126°–128°.

ANALYSIS: Calculated for C$_{16}$H$_{21}$N$_3$OS: 63.35%C, 6.98%H, 13.85%N; Found: 63.20%C, 6.89%H, 13.49%N.

EXAMPLE 7

4-(1,2-Benzisothiazol-3-yl)piperidine-1-carboximidic acid 2-diethylaminoethyl ester To a solution containing 2-diethylaminoethanol and sodium 2-diethylaminoethoxide (prepared from 0.05 g Na metal and 15 ml of 2-diethylaminoethanol), was added 4.0 g (0.016 mole) of 3-(1-cyano-4-piperidinyl)-1,2-benzisothiazole. The mixture was stirred and heated to 80° C., whereupon it turned into a solution. Heating was stopped and the reaction mixture was stirred at ambient temperature for 16 hours. Subsequently, dry ice was added, the alcohol was removed under a reduced pressure, and the residue was triturated with hexane to yield 5.2 g of a solid. Recrystallization from hexane yielded 3.7 g (64.1%) of the imidate as a solid, m.p. 84°–86°.

ANALYSIS: Calculated for C$_{19}$H$_{28}$N$_4$OS: 63.31%C, 7.83%H, 15.54%N; Found: 63.32%C, 7.78%H, 15.48%N.

I claim:

1. A compound of the formula

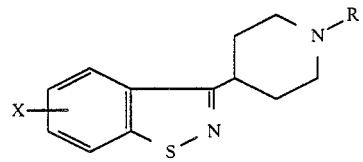

where X is hydrogen, halogen, loweralkoxy, loweralkyl, nitro, amino or trifluoromethyl; and R is

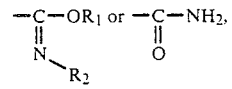

$R_1$ being loweralkyl, cycloalkylloweralkyl or a loweralkyl substituted with an amino, loweralkylamino or diloweralkylamino, and $R_2$ being hydrogen or loweralkyl; or a pharmaceutically acceptable acid addition salt thereof, the term cycloalkyl signifying an alicyclic group of 3 to 6 carbon atoms.

2. The compound as defined in claim 1 where X is hydrogen.

3. The compound as defined in claim 2 where R is

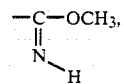

which is 4-(1,2-benzisothiazol-3-yl)piperidine-1-carboximidic acid methyl ester.

4. The compound as defined in claim 2 where R is

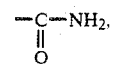

which is 3-(1-aminocarbonyl-4-piperidinyl-1,2-benzisothiazole.

5. The compound as defined in claim 2 where R is

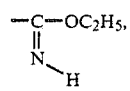

which is 4-(1,2-benzisothiazol-3-yl)piperidine-1-carboximidic acid ethyl ester.

6. The compound as defined in claim 2 where R is

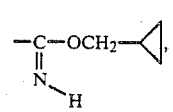

which is 4-(1,2-benzisothiazol-3-yl)piperidine-1-carboximidic acid cyclopropylmethyl ester.

7. The compound as defined in claim 2 where R is

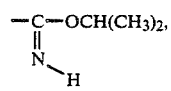

which is 4-(1,2-benzisothiazol-3-yl)piperidine-1-carboximidic acid 2-propyl ester.

8. The compound as defined in claim 2 where R is

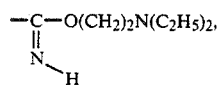

which is 4-(1,2-benzisothiazol-3-yl)piperidine-1-carboximidic acid 2-diethylaminoethyl ester.

9. A method of preparing a compound of the formula

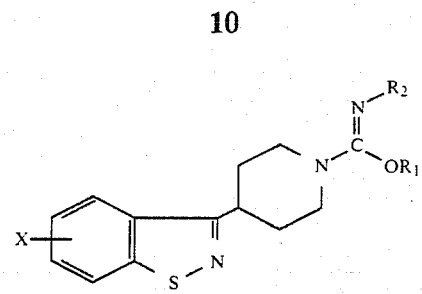

where X is hydrogen, halogen, loweralkoxy, loweralkyl, nitro, amino or trifluoromethyl; $R_1$ is loweralkyl, cycloalkylloweralkyl or a loweralkyl substituted with an amino, loweralkylamino or diloweralkylamino; and $R_2$ is a loweralkyl, the term cycloalkyl signifying an alicyclic group of 3 to 6 carbon atoms, which comprises:

(a) hydrolysis of a compound of the formula

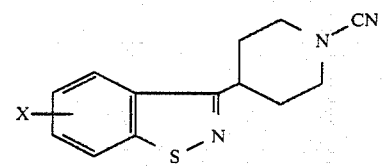

to afford a compound of the formula

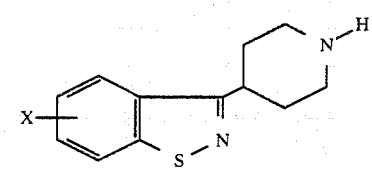

(b) reacting the above product with an isocyanate of the formula $R_2NCO$ to afford an urea derivative of the formula,

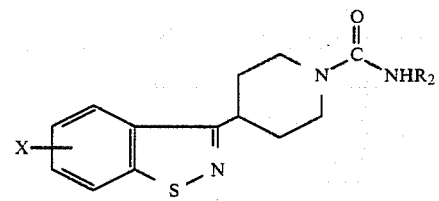

(c) reacting said urea derivative with $PCl_5$ to afford a chloro compound of the formula, and

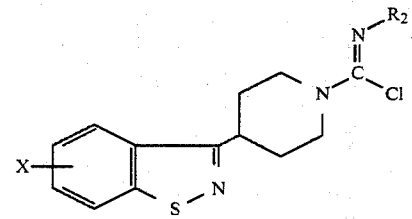

(d) reacting said chloro compound with the equivalent amount of an alkali metal alkoxide of alcohol $R_1OH$ to afford said target compound.

10. The method as defined in claim 9 where X is hydrogen.

11. A method of preparing a compound of the formula

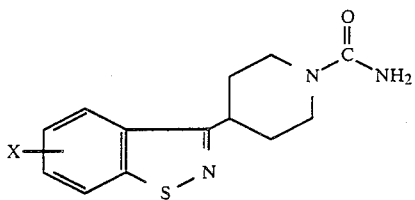

where X is hydrogen, halogen, loweralkoxy, loweralkyl, nitro, amino or trifluoromethyl, which comprises hydrolyzing a compound of the formula

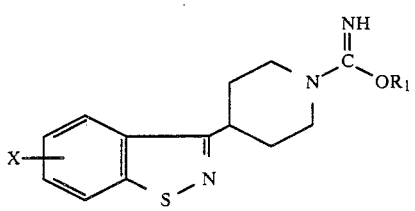

where R₁ is loweralkyl, cycloalkylloweralkyl or a loweralkyl substituted with an amino, loweralkylamino or diloweralkylamino to afford said compound, the term cycloalkyl signifying an alicyclic group of 3 to 6 carbon atoms.

12. The method as defined in claim 11 where X is hydrogen.

13. An antihypertensive composition comprising an effective amount of a compound of the formula

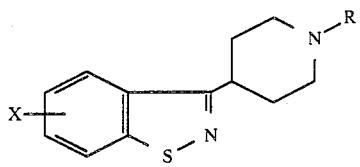

where X is hydrogen, halogen, loweralkoxy, loweralkyl, nitro, amino or trifluoromethyl; and R is

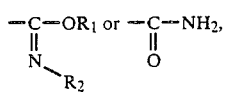

R₁ being loweralkyl, cycloalkylloweralkyl or a loweralkyl substituted with an amino, loweralkylamino or diloweralkylamino, and R₂ being hydrogen or loweralkyl; or a pharmaceutically acceptable acid addition salt thereof and an inert adjuvant, the term cycloalkyl signifying an alicyclic group of 3 to 6 carbon atoms.

* * * * *